United States Patent
Lowery et al.

(10) Patent No.: US 7,763,682 B2
(45) Date of Patent: *Jul. 27, 2010

(54) HYBRID INTRAOCULAR LENS MATERIALS FOR SMALL INCISION SURGERY

(75) Inventors: Michael D. Lowery, Vista, CA (US); Harish C. Makker, Mission Viejo, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 1109 days.

This patent is subject to a terminal disclaimer.

(21) Appl. No.: 11/390,804

(22) Filed: Mar. 27, 2006

(65) Prior Publication Data

US 2007/0225399 A1      Sep. 27, 2007

(51) Int. Cl.
*C08F 20/10* (2006.01)

(52) U.S. Cl. ............... 525/330.3; 525/288; 523/113; 523/106; 523/107; 623/4.1; 623/6.11; 623/6.17; 623/6.56; 623/6.58; 623/6.6

(58) Field of Classification Search ............ 523/113, 523/106, 107; 623/4.1, 6.11, 6.17, 6.56, 623/6.58, 6.6
See application file for complete search history.

(56) References Cited

U.S. PATENT DOCUMENTS

| | | | | |
|---|---|---|---|---|
| 4,954,586 | A * | 9/1990 | Toyoshima et al. | 526/245 |
| 6,555,030 | B1 * | 4/2003 | Weinschenk, III | 264/1.7 |
| 2005/0018310 | A1 * | 1/2005 | Kornfield et al. | 359/642 |
| 2005/0143751 | A1 * | 6/2005 | Makker et al. | 606/107 |
| 2006/0135642 | A1 * | 6/2006 | Makker et al. | 523/113 |

FOREIGN PATENT DOCUMENTS

WO    2006/002201 A2    1/2006

* cited by examiner

*Primary Examiner*—Vasu Jagannathan
*Assistant Examiner*—Robert C Boyle

(57) ABSTRACT

Intraocular lenses comprised of an acrylic-silicone hybrid polymer are disclosed. The intraocular lenses described herein are suitable for insertion through incisions of 2 mm or less.

15 Claims, No Drawings

HYBRID INTRAOCULAR LENS MATERIALS FOR SMALL INCISION SURGERY

FIELD OF THE INVENTION

The invention disclosed herein pertains to materials suitable for hydrophobic polymeric intraocular lenses capable of being inserted through small incisions.

BACKGROUND OF THE INVENTION

The human eye is a highly evolved and complex sensory organ. It is composed of a cornea, or clear outer tissue which refracts light rays enroute to the pupil, an iris which controls the size of the pupil thus regulating the amount of light entering the eye, and a lens which focuses the incoming light through the vitreous fluid in the eye to the retina. The retina converts the incoming light to electrical energy that is transmitted through the brain to the occipital cortex resulting in a visual image. In a perfect eye, the light path from the cornea, through the lens and vitreous fluid to the retina is unobstructed. Any obstruction or loss of clarity within these structures, however, causes scattering or absorption of light rays resulting in diminished visual acuity. For example, the cornea can become damaged resulting in edema, scarring or abrasions, the lens is susceptible to oxidative damage, trauma and infection, and the vitreous fluid can become cloudy due to hemorrhage or inflammation.

As the body ages, the effects of oxidative damage caused by environmental exposure and endogenous free radical production accumulate resulting in a loss of lens flexibility and an accumulation of denatured proteins that slowly coagulate reducing lens transparency. The natural flexibility of the lens is essential for focusing light onto the retina by a process referred to as accommodation. Accommodation allows the eye to automatically adjust the field of vision for objects at different distances. A common condition known as presbyopia results when the cumulative effects of oxidative damage diminish this flexibility reducing near vision acuity. Presbyopia usually begins to occur in adults during their mid-forties; mild forms are treated with glasses or contact lenses.

Lenticular cataracts are a lens disorder resulting from protein coagulation and calcification. There are four common types of cataracts: senile cataracts associated with aging and oxidative stress; traumatic cataracts which develop after a foreign body enters the lens capsule or following intense exposure to ionizing radiation or infrared rays; complicated cataracts which are secondary to diseases such as diabetes mellitus or eye disorders such as detached retinas, glaucoma and retinitis pigmentosa; and toxic cataracts resulting from medicinal or chemical toxicity. Regardless of the cause, the disease results in impaired vision and can lead to blindness.

Treatment of severe lens disease requires the lens' surgical removal or phacoemulsification followed by irrigation and aspiration. However, without a lens, the eye is unable to focus incoming light on the retina. Consequently, artificial lenses must be used to restore vision. Three types of prosthetic lenses are available: cataract glasses, external contact lenses and intraocular lenses (IOLs). Cataract glasses have thick lenses, are uncomfortably heavy and cause vision artifacts such as central image magnification and side vision distortion. Contact lenses resolve many of the problems associated with cataract glasses, but require frequent cleaning, are difficult to handle (especially for elderly patients with symptoms of arthritis), and are not suited for persons who have restricted tear production. Intraocular lenses are used in the majority of cases to overcome the aforementioned difficulties associated with cataract glasses and contact lenses.

There are four primary IOL categories: non-deformable, foldable, expansible hydrogels and injectable. Early non-deformable IOL implants were rigid structures composed of acrylates and methacrylates requiring a large incision in the capsular sac and were not accommodative. This large incision resulted in protracted recovery time and considerable discomfort for the patient. In an effort to reduce recovery time and patient discomfort numerous small incision techniques and IOLs have been developed.

Early IOLs designed for small incision implantation were elastomeric compositions that could be rolled or folded, inserted into the capsular sac and then unfolded once inside. Occasionally, the fold of the IOL before insertion resulted in permanent deformation adversely affecting the implant's optical qualities. Further, while foldable IOLs overcame the need for the large incision non-deformable IOLs required, foldable IOLs still were not accommodative. Moreover, both non-deformable and foldable IOLs are susceptible to mechanical dislocation resulting in damage to the corneal endothelium.

Another approach to small incision IOL implantation uses an elastomeric polymer that becomes pliable when heated to body temperature or slightly above. Specifically, the IOL is made pliable and is deformed along at least one axis reducing its size for subsequent insertion through a small incision. The IOL is then cooled to retain the modified shape. The cooled IOL is inserted into the capsular sac and the natural body temperature warms the IOL at which point it returns to its original shape. The primary drawback to this type of thermoplastic IOL is the limited number of polymers that meet the exacting needs of this approach. Most polymers are composed of polymethylacyrlate which have solid-elastomeric transition temperatures above 100° C. Modifications of the polymer substrate require the use of plasticizers that may eventually leach into the eye causing harmful effects.

Dehydrated hydrogels have also been used with small incision techniques. Hydrogel IOLs are dehydrated before insertion and naturally rehydrated once inside the capsular sac. However, once fully rehydrated the polymer structure is notoriously weak due to the large amount of water absorbed. The typical dehydrated hydrogel's diameter will expand from 3 mm to 6 mm resulting in an IOL that is 85% water. At this water concentration the refractive index (RI) drops to about 1.36 which is unacceptable for an IOL. To achieve a RI between 1.405 to 1.410 a significantly thicker lens is required.

Modern acrylate IOLs generally possess excellent mechanical properties such as foldability, tear resistance and physical strength. Moreover acrylate IOLs are known to possess superior optical properties (transparency) and are also highly biocompatible. However, pure acrylic IOLs having the desired combination of mechanical, optical and biological properties may have unacceptable molecular response times such that the folded or compacted IOL may not unfold quickly enough to prevent post-insertion complications when inserted through a 3 mm or less incision. A pure acrylate IOL fabricated to have a molecular response time sufficient to minimize post-insertion complications can be extremely tacky and lack the desired mechanical strength. In this case, the resulting IOL may tear easily and/or the resulting self-tack can prevent unfolding. Thus pure acrylate IOLs are generally not suitable for incision sizes of 2 mm or less.

Pure silicone IOLs generally possess excellent mechanical, optical and biological properties similar to pure acrylate IOLS. Moreover, silicones also possess excellent molecular response times; in fact, the silicone IOLs are so responsive that when folded small enough to be inserted through a 3 mm or less incision, the stored energy can be so great that the IOL unfolds explosively damaging delicate eye tissues and structures. Consequently, pure silicone IOLs are not suitable for insertion through 2 mm or less surgical incisions.

Therefore there remains a need for IOLs that combine desirable mechanical, optical and biological properties with the ability to be compacted or folded into shapes or sizes that permit insertion through 2 mm or less, incisions without risking adverse post insertion complications.

SUMMARY OF THE INVENTION

The present invention solves the aforementioned problems associated with pure acrylic and pure silicone intraocular lenses (IOLS) by providing IOLs comprising an acrylic-silicone hybrid material. The IOLs made in accordance with the teachings of the present invention possess properties that result in foldable, accommodating IOLs that are suitable for insertion through 2 mm or less incisions using a surgical inserter without damaging the IOL, the inserter cartridge or the surrounding ocular tissues.

These properties include, but are not limited to, hydrophobicity, a low initial modulus, a low modulus at intermediate elongation, a high modulus at full elongation, a high ultimate tensile strength and a controlled glass transition temperature (Tg).

In one embodiment of the present invention the IOL comprises acrylic-silicone hybrid materials having structural monomers selected from the group consisting of phenoxyethyl acrylate, ethyl acrylate, ethyl methacrylate, and combinations thereof, an unsaturated terminated silicone cross-linker and optionally, another cross-linker such as, but not limited to, ethylene glycol dimethacrylate or tetraethylene glycol dimethacrylate and combinations thereof.

In another embodiment of the present invention the IOL comprises an acrylic-silicone hybrid materials comprised of phenoxyethyl acrylate, ethyl acrylate, and ethyl methacrylate and an unsaturated terminated silicone cross-linker.

Moreover, the acrylic-silicone hybrid IOLs of the present invention are accommodating and their RIs can be matched to those of the natural crystalline lens. The natural RI of the eye is about 1.38 for light in the visible wavelengths. In the present invention, the implantable IOLs produced have RIs ranging from about 1.40 to about 1.56.

Thus, in one embodiment of the present invention a polymeric intraocular lens (IOL) material comprising at least one polymerizable acrylate monomer and an unsaturated terminated siloxane cross-linker, wherein said IOL material is used to provide an IOL that can be inserted through a 2 mm or less incision is provided wherein the acrylate monomer is selected from the group consisting of phenoxyethyl acrylate, ethyl acrylate, ethyl methacrylate and combinations thereof.

In another embodiment of the present invention the polymeric IOL material further comprises an additional cross-linker selected from the group consisting of ethylene glycol dimethyl acrylate, tetraethylene glycol dimethyl acrylate and combinations thereof.

The unsaturated terminated siloxane cross-linker used in accordance with the teachings of the present invention is selected from the group consisting of vinyl terminated siloxanes, methacrylate functional siloxanes, acrylate functional siloxanes and combinations thereof and specifically includes vinyl terminated siloxanes selected from the group consisting of vinyl terminated diphenylsiloxane-dimethylsiloxane copolymers, vinyl terminated polyphenylmethylsiloxanes, vinylphenylmethyl terminated vinylphenylsiloxane-phenylmethylsiloxane copolymers, vinyl terminated polydimethylsiloxanes and combinations thereof.

In one specific example of the present invention the vinyl terminated siloxane is:

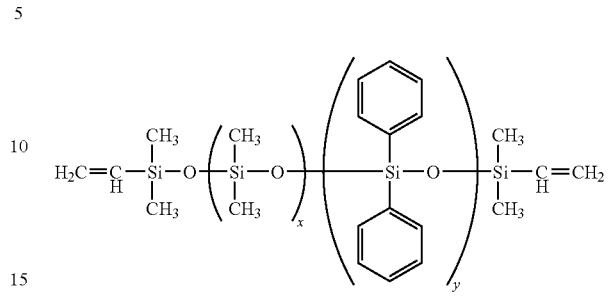

wherein x ranges from about 5 to about 10, and y ranges from about 3 to about 8 and the sum of x and y is equal to about 15.

In one embodiment of the present invention the polymeric IOL material comprises phenoxyethyl acrylate from about 45 to about 55 mass %, ethyl acrylate from about 15 to about 40 mass %, ethyl methacrylate from about 5 to about 25 mass % and an unsaturated terminated siloxane cross-linker from about 5 to about 10 weight %.

In yet another embodiment of the present invention the IOL is suitable for insertion through an incision of 2 mm or less and comprises a polymer wherein the polymer has a glass transition temperature of less than or equal to 10° C., a tensile strength between about 450 psi and 1250 psi, a percent elongation at break of greater than or equal to about 200%, a modulus at 100% of less than or equal to about 150 psi and optionally includes additional materials selected from the group consisting of an ultraviolet lights absorbing dye, a blue light absorbing dye and combinations thereof.

DEFINITION OF TERMS

To aid in understanding the following detailed description of the present invention, the terms and phrases used herein shall have the following, non-limiting, definitions.

Elongation: As used herein, "elongation" refers to the act of lengthening or stretching a polymeric material.

Full Elongation: As used herein, "full elongation" refers to the act of lengthening or stretching a polymeric material or polymeric IOL to its limit.

Intermediate Elongation: As used herein, "intermediate elongation" refers to the act of lengthening or stretching a polymeric material or polymeric IOL to a point between its original length and limit.

Glass Transition Temperature (Tg): As used herein, the "glass transition temperature (Tg)" refers to the temperature wherein a polymeric material becomes less elastic and more brittle.

Mass percent: As used herein, "mass percent" and "mass %" refer to the mass of monomer present in a polymer divided by the total weight of the polymer multiplied by 100. Mathematically mass percent is represented by the following formula where $M_m$ is the mass of the monomer and $M_P$ is the mass of the corresponding polymer: $[M_m/M_P] \times 100 =$ Mass Percent.

Modulus: As used herein, "modulus" refers to the physical measurement in pounds per square inch (psi) of stiffness in a material, equaling the ratio of applied stress to the resultant deformation of the material, such as but not limited to elasticity or shear.

Moduli: As used herein, "moduli" refers to the plural form of modulus.

Percent Elongation: As used herein, "percent elongation" refers to the length of an elongated polymer divided by the length of the original polymer. Mathematically the percent elongation is represented by the following formula where L is the length of the elongated polymer and $L_0$ is the length of the non-elongated corresponding polymer: $[L/L_0] \times 100 =$ Percent Elongation.

Pliable: As used herein, "pliable" refers to the flexible nature of a polymeric material and to the flexibility of polymeric IOLs that can be folded, rolled or otherwise deformed sufficiently to be inserted through a 2 mm or less surgical incision.

psi: As used herein, "psi" refers to pounds per square inch, a unit of pressure or stress.

2 mm or less surgical incision: As used herein, "2 mm or less surgical incision" refers to a surgical incision in the cornea, sclera or limbus of the eye.

Resiliency: As used herein, "resiliency" refers to a polymeric material or a polymeric IOL's inherent ability to return to its pre-stressed configuration following impact, deformation in an inserter and the resulting deformation associated with the stress on impact, also referred to herein after as "rebound resiliency."

Refractive Index (RI): As used herein, "refractive index (RI)" refers to a measurement of the refraction of light an IOL. More specifically, it is a measurement of the ratio of the speed of refracted light in a vacuum or reference medium to its speed in the medium under examination Softness: As used herein, "softness" refers to a polymeric material or a polymeric IOL's resilience and pliability as opposed to e.g. a polymethylmethacrylate (PMMA) IOL that is rigid and hard.

Ultimate Tensile Strength: As used herein, "ultimate tensile strength" refers to the maximum stress in psi a material can withstand.

DETAILED DESCRIPTION OF THE INVENTION

The present invention is directed to intraocular lenses (IOLs) suitable for insertion-through incisions of 2 mm or less. Therefore, it is desirable to have IOLs that can be folded, rolled or otherwise deformed such that they can be inserted through small incisions. Furthermore, in order to minimize patient trauma and post surgical recovery time the IOL must comprise a responsive polymer that unfolds controllably. To meet these requirements, the polymers must have minimum self tack and must not retain excessive amounts of stored mechanical energy. However, if the IOL is too thin, or the polymer lacks sufficient mechanical strength, it may be extremely fragile and easily dislocated or damaged during or after the insertion process.

Historically foldable IOL materials have been designed to be tough (tensile strength of greater than 750 pounds per square inch [psi]) and with a relatively high percent elongation (greater than 100%). These properties give the IOL sufficient toughness such that the IOL does not tear from the forces experienced during insertion through a 2.6 to 3.2 incision. These properties are important, however, the mechanical properties of most of the hydrophobic IOL materials currently on the market clearly preclude their use in 2 mm or less incision surgery using conventional insertion systems. For example, presently available prior art foldable IOLs include Sensar® (Advanced Medical Optics, Santa Ana Calif.), an acrylic IOL having a tensile strength of about 850 psi and an elongation at break of about 140%; SLM-2® (Advanced Medical Optics, Santa Ana Calif.), a silicone IOL having a tensile strength of about 800 psi and an elongation at break of about 230%; and AcrySof® (Alcon Laboratories, Fort Worth, Tex.) having a tensile strength of about 1050 psi. All three IOLs are suitable for insertion through incision sizes of about 2.6 mm or greater, but to date, no hydrophobic acrylic IOL has been developed that can be inserted through 2 mm or less incisions without damaging either the eye or the IOL.

Hydrophobic acrylic materials offer numerous advantages over silicone or hydrogel materials for IOL production. First, a large number of high purity, optical grade acrylate/methacrylate monomers are commercially available. The flexibility of monomer selection provides for control over the material's mechanical, optical and thermal properties. For example, the ability to adjust the material's refractive index (RI) and mechanical properties is important in designing ultra-small incision IOLs. Secondly, hydrophobic acrylics have demonstrated excellent ocular biocompatibility. Hydrogels are prone to calcification and the market is generally turning away from silicone IOLs in favor of acrylics. However, as discussed, pure acrylic IOLs that have the requisite physical, mechanical and optical properties required to develop a 2 mm or less incision IOL have not been developed. Thus, the present inventors have surprisingly discovered that by combining suitable amounts of silicone materials into acrylic IOL materials, an IOL can be made that has the properties required to pass through a 2 mm or less incision without damage to the IOL, the inserter cartridge or the eye.

Silicones have unique properties derived from the inherent flexibility of the siloxane bond. The alternating silicon-oxygen polymer backbone of siloxanes makes them remarkably more flexible than their organic counterparts that have a carbon-oxygen backbone. This property of siloxanes results in low glass-transition temperatures (Tg) and excellent flexibility. Furthermore, a low initial modulus is another important attribute that siloxanes contribute to the acrylic-silicone hybrids of the present invention. A conventional refractive IOL must elongate up to about 100% in order to pass through the insertion cartridge. Therefore, it is important that the initial modulus be optimally low. A low initial modulus translates to low stimulus required to express the IOL through the cartridge. Thus, when appropriate amounts of selected siloxanes are incorporated into an acrylic structural polymer, the resulting acrylic-silicone hybrid IOLs have the flexibility, Tg and modulus required to make a refractive IOL suitable for insertion through a 2 mm or less incision without harming the IOL, the inserter cartridge or the eye.

The acrylic-silicone hybrid materials made in accordance with the teachings of the present invention have low initial moduli, high ultimate tensile strength, a controlled glass transition temperature (Tg) (about 5° C. to about 15° C.), and high moduli at full elongation (greater than about 250% elongation). Moreover the IOLs of the present invention may be multifocal (i.e. refractive or diffractive), accommodating (i.e. deformable or movable under the normal muscle movements of the human eye), highly biocompatible and have RIs ranging from about 1.40 to about 1.56 for light in the visible wavelengths.

The present inventors achieve these and other objects of the invention by providing novel acrylic based hydrophobic polymers comprising structural monomers selected from the group consisting of phenoxyethyl acrylate, ethyl acrylate and ethyl methacrylate and crosslinked using an unsaturated terminated silicone. Optionally, at least one additional crosslinker may be used such as, but not limited to, ethylene glycol dimethacrylate and tetraethylene glycol dimethacrylate.

The unsaturated terminated siloxanes can include vinyl terminated siloxanes or methacrylate and acrylate functional siloxanes. Non-limiting examples include vinyl terminated diphenylsiloxane-dimethylsiloxane copolymers, vinyl terminated polyphenylmethylsiloxanes, vinylphenylmethyl terminated vinylphenylsiloxane-phenylmethylsiloxane copolymers, vinyl terminated polydimethylsiloxanes and methacrylate and acrylate functional siloxanes. Representative materials can be obtained from Gelest, Inc. (Morrisville, Pa.) or synthesized using methods known to those skilled in the art of silicone chemistry.

In one embodiment of the present invention the unsaturated terminated siloxane is a vinyl terminated siloxane having the structure as depicted Formula 1 below (referred to herein as "AMO silicone fluid"). The values for "x" and "y" will vary depending on the refractive index of the lens. For example, if an IOL having refractive index of 1.52 is desired, the "x:y" ratio may be approximately 5:3, a ratio of "x" to "y" equal to 3:1 will give an IOL having a RI of approximately 1.50. However, regardless of the ratio of "x" to "y" the total x+y should not exceed 40 or the lens may become opaque and thus not acceptable as an IOL. Furthermore, if the "y" component becomes too dominant (>90%) the lens material may become increasingly stiff and thus not suitable for a sub 2 mm incision. Thus persons having ordinary skill in the art of polymer chemistry and optics can prepare an IOL having the desired RI, optical clarity and mechanical properties by adjusting the x:y ratio using skills known in the art without undue experimentation. In one embodiment of the present invention x ranges from about 5 to about 10, and y ranges from about 3 to about 8 and the sum of x and y is equal to about 15.

Formula 1

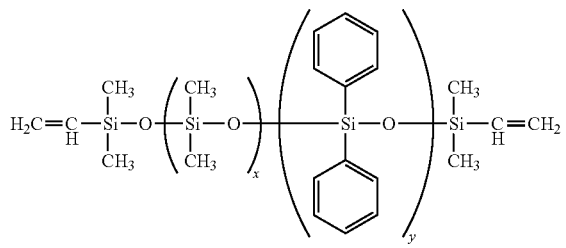

Optionally a number of ultraviolet (UV) and blue light absorbing dyes can be added to the hybrid acrylic-silicone polymers of the present invention. For example, the hybrid acrylic-silicone IOLs of the present invention may include 1.0 to 1.5 mass % of UV and blue light absorbing compounds such as benzophenone and benzotriazole-based UV light absorbers or blue light blocking dyes including azo and methine yellow dyes that selectively absorb UV/blue light radiation up to about 450λ. See for example U.S. Pat. Nos. 5,374,663; 5,528,322; 5,543,504; 5,662,707; 6,277,940; 6,310,215 and 6,326,448, the entire contents of which are incorporated herein by reference for all they teach regarding UV and blue light absorbing dyes.

A variety of initiators for polymerization reactions are employed in the present invention. In one embodiment of the present invention, and not intended as a limitation, peroxide initiators are used. Examples of peroxide initiators include, without limitation, about 0.100 to about 1.50 mass % of di-tert-butyl peroxide (Trigonox® a registered trademark of Akzo Chemie Nederland B.V. Corporation Amersfoort, Netherlands) or 2,5-dimethyl-2,5-bis(2-ethylhexanoylperoxy) hexane.

The present invention provides acrylic-silicone hybrid polymeric materials useful for making hydrophobic polymeric IOLs that can be inserted through 2 mm or less incisions without damaging the IOL or delicate eye structures surrounding it. The acrylic-silicone hybrids of the present invention possess low initial modulus, low modulus at intermediate elongation, high modulus at full elongation, high ultimate tensile strength, and controlled Tgs. The glass transition temperature (Tg) should be from about 0° C. to about 10° C. to provide a non-brittle polymer that is readily folded and manipulated. A low initial modulus provides for a more easily inserted IOL by reducing the force required to express the hydrophobic acrylic-silicone hybrid polymer IOL through the inserter cartridge. Lens rupture and permanent deformation is minimized by providing an acrylic-silicone hybrid having a high ultimate tensile strength and high modulus at full elongation.

EXAMPLES

Example 1

Synthesis of a Acrylic-Silicone Hybrid

In one method for making the biocompatible polymers of the present invention, a reaction mixture is prepared in a suitable reaction vessel such as a one liter three-neck round-bottom flask by carefully mixing about 50 mass % phenoxyethyl acrylate (PEA), about 10 mass % ethyl methacrylate (EMA), about 30 mass % ethylacrylate (EA), about 9 mass % of AMO silicone fluid, about 0.3 mass % ethyleneglycol dimethacrylate (EGDMA), about 1 mass % of a suitable thermal initiator, such as a peroxide including but not limited to di-tert-butyl peroxide (Trigonox® a registered trademark of Akzo Chemie Nederland B.V. Corporation Amersfoort, Netherlands) and/or 2,5-dimethyl-2,5-bis(2-ethylhexanoylperoxy) hexane) and about 0.25 mass % of UVAM. The thermal initiator is generally added last after the reaction vessel is securely supported and provided with a mixing means such as a magnetic stir plate with stir bar or a low-shear impeller and overhead drive. Next nitrogen gas is gently (≈1 PSI) bubbled through the reaction mixture for about 15 minutes and the reaction mixture is degassed under vacuum for five minutes. Because thermal initiated polymerization is exothermic, it is important to maintain control over the reaction mixture. An immersion chiller water bath can be used to prevent the reaction mixture from overheating.

Example 2

Forming the IOL from the Acrylic-Silicone Hybrid

The IOLs of the present invention are formed by transferring the biocompatible polymer reaction mixture into molds having the desired shape before the polymerization and cross-linking reactions are complete. In one embodiment of the present invention, molds are provided to receive the liquid reaction mixture. The molds are first brought to a suitable temperature that permits the polymer IOL material to cure in a controlled manner. In one embodiment of the present invention, a water bath is used to maintain mold temperature at about 80° C.±2° C. One non-limiting method for transferring the reaction mixture to the molds is by increasing the pressure in the reaction vessel relative to atmospheric pressure and providing a route for the pressurized reaction mixture to exit the reaction vessel. In one embodiment of the present invention nitrogen gas is pumped into the reaction vessel and the reaction mixture is forced from the reaction vessel through an appropriate grade of tubing. As the reaction mixture exits the reaction vessel it is passed though a filter into the mold. The filled mold is then transferred to a water bath maintained at 74±4° C. and allowed to stay there for about 16 to about 24 hours. Next the molds are transferred to a dry heat curing oven equilibrated to about 90° C. The molds are held at this temperature for an additional 16 to 24 hours. At this point, solid, soft acrylic polymer sheets are ready to be processed further to form IOLs having various diopters as known to those skilled in the art.

was employed in these experiments to simulate a sub 2 mm insertion process. A viscoelastic lubricant (Healon® 10 mg/mL of sodium hyaluronate 5000) was used to lubricate the inserter tube consistent with normal clinical practice. Testing was performed at 18° C. The IOLs were then extruded using the same force generally used in clinical practice and then inspected for physical damage and optical performance. The inserter cartridge was also inspected for damage post extrusion. As can be seen in the data presented in Table 3, neither the lenses nor the inserter cartridge was damaged during the insertion process and the IOLs were optically acceptable post extrusion. Thus, the data presented in Table 3 establishes that the acrylic-silicone hybrid IOLs made in accordance with the teachings of the present invention can be inserted into a sub 2 mm incision without damaging the IOL or distorting its optical qualities. Moreover, the inserter was not damaged during the insertion process indicating that the insertion procedure does not require excessive torque and thus eye trauma is unlikely to occur.

TABLE 1

Exemplary Embodiments of the Present Invention

| Formulation for Silicone-acrylic Hybrid | DL21-1 | DL21-2 | DL28-1 | DL28-2 | DL28-4 | EH22-4 | EH22-2 |
|---|---|---|---|---|---|---|---|
| Phenoxyethyl acrylate | 50.0% | 50.0% | 50% | 50.0% | 50.0% | 49.0% | 49.0% |
| Ethyl acrylate | 30.0% | 30.0% | 20% | 38.0% | 30.0% | 29.5% | 29.5% |
| Ethyl methacrylate | 10.9% | 14.0% | 21% | 6.0% | 10.9% | 10.7% | 10.7% |
| AMO ® Silicone Fluid | 9.1% | 6.0% | 9% | 6.0% | 9.1% | — | — |
| Gelest PVV-3522 | — | — | — | — | — | 8.9% | — |
| Gelest DMS-R11 | — | — | — | — | — | — | 8.9% |
| Ethyleneglycol dimethacrylate | 0.3% | 0.1% | 0.3% | 1.0% | 0.1% | 0.3% | 0.3% |
| Tetraethyleneglycol dimethacrylate | 0.0% | 0.5% | 0.3% | — | 0.5% | — | — |
| Trigonox-141 | 1.0% | 1.0% | 1.0% | 1.0% | 1.0% | 1.0% | — |
| Trigonox-C | 0.5% | 0.5% | 0.5% | 0.5% | 0.5% | 0.5% | — |

TABLE 2

Mechanical Properties of the Exemplary Embodiments of the Present Invention

| Formulation for Silicone-acrylic/Mechanical Property | DL21-1 | DL21-2 | DL28-1 | DL28-2 | DL28-4 | EH22-4 | EH22-2 |
|---|---|---|---|---|---|---|---|
| Tensile at Break (psi) | 883 | 771 | 1210 | 481 | 693 | 1257 | 399 |
| Elongation at Break (%) | 314 | 259 | 262 | 255 | 280 | 157 | 115 |
| Modulus at 30% (psi) | 190 | 316 | 953 | 261 | 231 | 422 | 240 |
| Modulus at 50% (psi) | 139 | 220 | 584 | 122 | 167 | 335 | 227 |
| Modulus at 100% (psi) | 97 | 143 | 334 | 1.0% | 112 | 390 | 262 |

Table 3 below presents performance results of IOLs made in accordance with the teachings of the present invention. Acrylic-silicone hybrid IOLs having different diopters where folded and placed in IOL inserter cartridges. The folded IOLs were held in the "wing" portion of the inserter (W) from 0 to 4 minutes before being advanced into the inserter tube (T) where they were held from 0 to 1 minute before being extruded from the cartridge tip. A 1.6 mm bore cartridge tube

TABLE 3

IOL performance data when passed through a sub 2 mm inserter

| Run Number | IOL diopter | Dwell time in Inserter W | Dwell time in Inserter T | Torque Applied to IOL in g-cm | IOL performance | Cartridge performance | Optical Performance post extrusion |
|---|---|---|---|---|---|---|---|
| 1 | 30 | 0 | 1 | 200 | ok | ok | Ok |
| 2 | 30 | 0 | 1 | 150 | ok | ok | Ok |
| 3 | 30 | 0 | 0 | 175 | ok | ok | Ok |
| 4 | 30 | 0 | 0 | 150 | ok | ok | Ok |
| 5 | 30 | 0 | 0 | 180 | ok | ok | Ok |
| 6 | 30 | 2 | 0 | 200 | ok | ok | Ok |

TABLE 3-continued

IOL performance data when passed through a sub 2 mm inserter

| Run Number | IOL diopter | Dwell time in Inserter W | T | Torque Applied to IOL in g-cm | IOL performance | Cartridge performance | Optical Performance post extrusion |
|---|---|---|---|---|---|---|---|
| 7 | 30 | 2 | 0 | 200 | ok | ok | Ok |
| 8 | 30 | 2 | 0 | 175 | ok | ok | Ok |
| 17 | 6 | 0 | 1 | 150 | ok | ok | Ok |
| 18 | 20 | 0 | 1 | 190 | ok | ok | Ok |
| 19 | 6 | 2 | 0 | 180 | ok | ok | Ok |
| 20 | 20 | 2 | 0 | 225 | ok | ok | Ok |
| 21 | 6 | 2 | 1 | 190 | ok | ok | Ok |
| 22 | 20 | 2 | 1 | 200 | ok | ok | Ok |
| 23 | 6 | 4 | 1 | 180 | ok | ok | Ok |
| 24 | 20 | 4 | 1 | 180 | ok | ok | Ok |

Some exemplary polymers and their chemical compositions used to prepare hydrophobic IOL materials according to the teachings of the present invention are summarized in Table 1. The table describes the mass percents of monomers used for synthesizing hydrophobic polymeric materials suitable for IOLs that are inserted through 2 mm or less surgical incisions. It is understood that the mass percents in Table 1 are approximate and that minor amounts of solvent and residual reactants can remain in the IOL material. It is also understood that the mass percents are relative and where additional material such as UV and blue light blocking dyes are added, the mass percents are necessarily adjusted in a relative fashion to account for the additional materials such that the total mass percent equals 100%. Thus the term "about" is used to provide for variance in measuring accuracy as well as to account for the small additional amounts of optional ingredients such as dyes and cross-linkers when the total mass percent would otherwise exceed 100%.

Depicted in Table 2 are mechanical properties of exemplary polymers depicted in Table 1. The moduli and tensile strengths are expressed in psi. The properties depicted in Table 2 favorably support the requirements for hydrophobic polymeric materials suitable for IOLs that are inserted through 2 mm or less surgical incisions. Thus, the physical and mechanical parameters exhibited by the acrylic-silicone IOLs of the present invention should be a Tg less than or equal to 10° C.; tensile strengths between about 450 psi and 1250 psi, a percent elongation at break of greater than or equal to about 200% a modulus at 100% of less than or equal to about 150 psi.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Certain embodiments of this invention are described herein, including the best mode known to the inventors for carrying out the invention. Of course, variations of these embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A polymeric intraocular lens (IOL) material comprising:
at least one polymerizable acrylate monomer and an unsaturated terminated siloxane cross-linker, wherein the unsaturated terminated siloxane cross-linker is

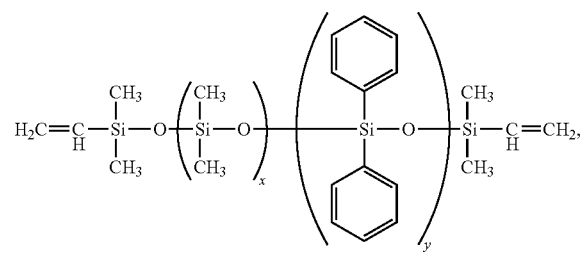

wherein x ranges from about 5 to about 10, and y ranges from about 3 to about 8 and the sum of x and y is equal to about 15, and wherein said IOL material is used to provide an IOL that can be inserted through a 2 mm or less incision, wherein the material is made by mixing the at least one polymerizable acrylate monomer and unsaturated terminated siloxane cross-linker to form a mixture.

2. A polymeric IOL material as recited in claim 1 wherein said acrylate monomer is selected from the group consisting of phenoxyethyl acrylate, ethyl acrylate, ethyl methacrylate and combinations thereof.

3. A polymeric IOL material as recited in claim 1 wherein said IOL material further comprises an additional cross-linker selected from the group consisting of ethylene glycol dimethyl acrylate, tetraethylene glycol dimethyl acrylate and combinations thereof.

4. A polymeric IOL material as recited in claim 2 wherein the composition of phenoxyethyl acrylate is from about 45 to about 55 mass %, said ethyl acrylate is from about 15 to about 40 mass %, said ethyl methacrylate is from about 5 to about 25 mass % and said unsaturated terminated siloxane cross-linker is from about 5 to about 10 weight %.

5. The polymeric intraocular lens (IOL) material according to claim 1 wherein said IOL additionally contains an additional material selected from the group consisting of an ultraviolet light absorbing dye, a blue light absorbing dye and combinations thereof.

6. The polymeric intraocular lens (IOL) material of claim 1, wherein after the at least one polymerizable acrylate monomer and unsaturated terminated siloxane cross-linker are mixed to form a mixture, the mixture is cured via a single reaction step.

7. An intraocular lens (IOL) comprising:
a polymer comprising about 50 mass % phenoxyethyl acrylate, about 30 mass % ethyl acrylate, about 11% ethyl methacrylate and about 9% of an unsaturated terminated siloxane cross-linker, wherein the unsaturated terminated siloxane cross-linker is

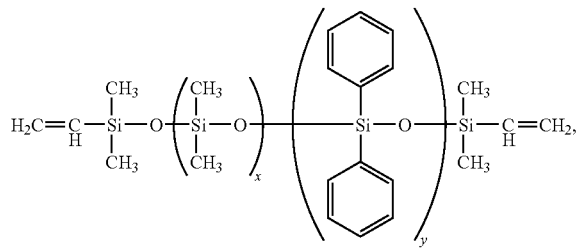

wherein x ranges from about 5 to about 10, and y ranges from about 3 to about 8 and the sum of x and y is equal to about 15, and wherein said IOL can be inserted through a 2 mm or less incision, wherein the polymer is made by mixing the phenoxyethyl acrylate, ethyl acrylate, ethyl methacrylate and unsaturated terminated siloxane cross-linker to form a mixture.

8. The IOL according to claim 7 wherein said IOL also comprises about 0.3 ethyleneglycol dimethacrylate as a cross-linker.

9. The intraocular lens (IOL) of claim 7, wherein said IOL additionally contains an additional material selected from the group consisting of an ultraviolet light absorbing dye, a blue light absorbing dye and combinations thereof.

10. The intraocular lens (IOL) of claim 7, wherein after the phenoxyethyl acrylate, ethyl acrylate, ethyl methacrylate and unsaturated terminated siloxane cross-linker are mixed to form a mixture, the mixture is cured via a single reaction step.

11. A intraocular lens (IOL) suitable for insertion through an incision of 2 mm or less wherein said IOL comprises a polymer wherein said polymer comprises at least one polymerizable acrylate monomer and an unsaturated terminated siloxane cross-linker, wherein the unsaturated terminated siloxane cross-linker is

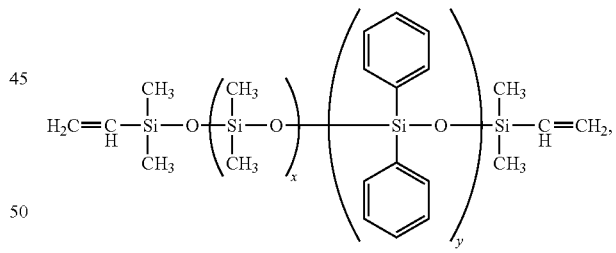

wherein x ranges from about 5 to about 10, and y ranges from about 3 to about 8 and the sum of x and y is equal to about 15; wherein the polymer has a glass transition temperature of less than or equal to 10° C., a tensile strength between about 450 psi and 1250 psi, a percent elongation at break of greater than or equal to about 200% and a modulus at 100% of less than or equal to about 150 psi; and wherein the polymer is made by mixing the at least one polymerizable acrylate monomer and unsaturated terminated siloxane cross-linker to form a mixture.

12. The IOL according to claim 11 wherein said acrylate monomer is selected from the group consisting of phenoxyethyl acrylate, ethyl acrylate, ethyl methacrylate and combinations thereof.

13. The IOL according to claim 11 wherein said IOL material further comprises an additional cross-linker selected from the group consisting of ethylene glycol dimethyl acrylate, tetraethylene glycol dimethyl acrylate and combinations thereof.

14. The IOL according to claim 11 wherein said IOL additionally contains an additional material selected from the group consisting of an ultraviolet light absorbing dye, a blue light absorbing dye and combinations thereof.

15. The intraocular lens (IOL) of claim 11, wherein after mixing the at least one polymerizable acrylate monomer and unsaturated terminated siloxane cross-linker to form a mixture, the mixture is cured via a single reaction step.

* * * * *

UNITED STATES PATENT AND TRADEMARK OFFICE
Certificate

Patent No. 7,763,682 B2                                        Patented: July 27, 2010

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Michael D. Lowery, Vista, CA (US); Harish C. Makker, Mission Viejo, CA (US); and Can B. Hu, Irvine, CA (US).

Signed and Sealed this First Day of January 2013.

VASU JAGANNATHAN
*Supervisory Patent Examiner*
Art Unit 1764
Technology Center 1700